(12) United States Patent
Robbins

(10) Patent No.: US 6,928,862 B1
(45) Date of Patent: Aug. 16, 2005

(54) METHOD OF MONITORING DUAL-PHASE LIQUID AND INTERFACE LEVELS

(76) Inventor: Bryce V. Robbins, P.O. Box 11568, Marina del Rey, CA (US) 90295-7568

( * ) Notice: Subject to any disclaimer, the term of this patent is extended or adjusted under 35 U.S.C. 154(b) by 154 days.

(21) Appl. No.: 10/729,182

(22) Filed: Dec. 4, 2003

(51) Int. Cl.$^7$ ............................................. G01N 13/00
(52) U.S. Cl. ...................... 73/64.55; 73/61.47; 73/299; 73/309; 73/321
(58) Field of Search ........................... 73/64.55, 61.54, 73/61.47, 61.78, 309, 319, 321, 299

(56) References Cited

U.S. PATENT DOCUMENTS

| | | | | |
|---|---|---|---|---|
| 3,935,741 | A * | 2/1976 | Zinsmeyer et al. | 73/313 |
| 4,348,278 | A * | 9/1982 | Caccia | 210/86 |
| 4,669,309 | A * | 6/1987 | Cornelius | 73/299 |
| 4,976,146 | A * | 12/1990 | Senghaas et al. | 73/313 |
| 5,347,864 | A * | 9/1994 | Senghaas et al. | 73/313 |
| 5,829,303 | A * | 11/1998 | Fraser | 73/319 |
| 5,874,899 | A * | 2/1999 | Barmore et al. | 340/623 |
| 5,950,487 | A * | 9/1999 | Maresca et al. | 73/293 |
| 6,217,752 | B1 * | 4/2001 | Coots | 210/66 |
| 2004/0093942 | A1 * | 5/2004 | Brun | 73/301 |

FOREIGN PATENT DOCUMENTS

| EP | 949487 A1 * | 10/1999 | G01F 23/00 |
|---|---|---|---|
| GB | 2029022 A * | 3/1980 | G01F 23/14 |

* cited by examiner

Primary Examiner—Hezron Williams
Assistant Examiner—John Fitzgerald
(74) Attorney, Agent, or Firm—The Kline Law Firm

(57) ABSTRACT

A dual-phase level monitoring (DPLM) instrument that provides continuous signals that enables determination of the location of the top surface of the lighter of two immiscible fluids (the product) and the hydrostatic pressure below the total fluid column of both immiscible fluids. By knowing the fluid specific gravities, the output signals are processed to yield the location of the air/product and liquid/liquid interfaces, and the depth of the lighter phase. The instrument is intended for use in groundwater monitoring wells with a light non-aqueous phase liquid (product) and tanks or vessels with dual-phase liquids and level monitoring and/or control issues. The DPLM instrument includes a first pressure transducer situated beneath the surface of the liquid with a greater specific gravity, which will typically be ground water. A level element with a float selected so as to be buoyant and float on the surface of the lighter fluid is positioned above the first pressure transducer. A signal from the level element is proportional to the position of the float or the total distance the float is positioned above the bottom of the level element and therefore the total distance above the first pressure transducer, the pressure transducer located in the heaver liquid phase. A second pressure transducer can be deployed above the surface of the liquid if greater accuracy of measurement (as compared to assuming ambient pressure) is desired.

7 Claims, 3 Drawing Sheets

METHOD OF MONITORING DUAL-PHASE LIQUID AND INTERFACE LEVELS

BACKGROUND OF THE INVENTION

1. Field of the Invention

The present invention relates generally to methods of measuring levels of liquids, and more particularly is method utilizing an automatic dual-phase instrument for continuously monitoring a dual-phase reservoir.

2. Description of the Prior Art

Currently, only manual measuring techniques are commonly used to measure liquid levels in a reservoir containing at least two immiscible liquids, such as in environmental monitoring wells. In environmental monitoring wells, it is desirable to measure the thickness of a free-product (product) layer, the depth-to-product (dtp), and the depth-to-groundwater (dtw). The measurements are most typically performed using a manual interface probe. The interface probe consists of a sensor attached to a signal/support cable (which is typically marked in graduations of 0.01 feet) that is wound around a hand reel. The sensor is capable of differentiating between the free-product and groundwater. As the sensor passes into and through each layer of liquid, the interface probe signals the operator audibly and/or visually. The interface probe signal differs depending on whether the sensor is detecting air, product, or water. The operator notes the dtp and dtw by checking the amount of cable that has been unrolled when the instrument indicates that the sensor has passed through the air/product interface and the product/groundwater interface. The operator can then easily calculate the thickness of the free-product layer. While fairly accurate, manually taking the measurements does not provide continuous monitoring, and is time consuming and tedious.

There are many devices disclosed in the prior art that measure, monitor, and control single phase liquids. One such measuring device is the "Fluid Level Monitor" of Yekutiely, et al., U.S. Patent Application # 20020029633, published Mar. 14, 2002. This device is able to monitor depth of a liquid by measuring the tensile force in a filament and a rotation of a spool around which the filament is wound.

The "Digital Electronic Liquid Density/Liquid Level Meter" of Articolo, George A., U.S. Patent Application # 20010029782, published Oct. 18, 2001, discloses a device that requires only a single float to directly and continuously measure a liquid level. The Articolo device can be used to determine specific gravity if two floats are used together.

The "Method and Apparatus for Controlling the Level of Liquids" by Molina, et al., U.S. Patent Application # 20030131661, published Jul. 17, 2003, discloses a method of accurately monitoring the level of a liquid in a container by correcting for the variation of the specific gravity values with temperature.

"Liquid Level Detection" by Fryer, et al., U.S. Pat. No. 5,094,102, issued Mar. 10, 1992, teaches a method and apparatus to monitor a liquid level in a bore hole and to activate a signal when the level reaches a monitor point.

The "Liquid Level Detector" of Toon, et al. U.S. Pat. No. 4,989,452, issued Feb. 5, 1991, discloses a probe that is lowered into a water well of other vessel and uses conductivity measuring electrodes to distinguish between the phases of liquid in the well. The device has an optical sensing facility to locate the top level of the liquid phase.

Finally, there are also some references directed to measuring the levels in a dual-phase vessel. One such reference is the "Method of Accurately Gauging Groundwater and Nonaqueous Phase Liquid Contaminants which Eliminates Cross Contamination Between Wells" by Milone, Christopher J., U.S. Patent Application # 20030041662, published Mar. 6, 2003. This method teaches the use of a dedicated detector (a conductive and hydrostatic resistive circuit) formed on a thin-film tape affixed to the wall of a well casing. The use of a dedicated detector does avoid cross contamination from the probe, however, the affixing of the detector at a given location limits the versatility of the device. This drawback is particularly limiting in applications in which multiple locations need to be tested, such as in field pilot-testing. Moreover, the inability to remove the device from the well makes service on the device difficult if not impossible.

Another dual-phase measuring device is the "Level Sensor" of Zinsmeyer, et al., U.S. Pat. No. 3,935,741, issued Feb. 3, 1976. The Zinsmeyer device uses a pair of magnets mounted in floats, each float being calibrated (by selecting the density of the material of the float) to float on one of two immiscible liquids. The floats are joined by a mechanical linkage, and as the liquid levels change the floats move coded tapes which are monitored by an optical reader. While this method is useful for measurements taken in tanks, the mechanical linkage of the two floats makes the system impractical for deep-well applications. The requirement for an optical reader also makes the Zinsmeyer method difficult to implement for in-well or on-well applications.

Accordingly, it is an object of the present invention to provide a removable and serviceable device to continuously measure the levels of dual-phase liquids.

It is another object of the present invention to provide a device that can be used in deep-well and small diameter well applications.

SUMMARY OF THE INVENTION

The present invention is a dual-phase level monitoring (DPLM) instrument that provides continuous signals of the level of the lighter of two immiscible fluids (the product) and the hydrostatic pressure below the fluid column. The DPLM instrument can optionally provide a continuous signal indicating the pressure in the air above the fluid column. Output signals are processed to yield the location of the air/product and liquid/liquid interfaces, and the depth of the lighter phase. The instrument is intended for use in groundwater monitoring wells with a light non-aqueous phase liquid (product) and tanks or vessels with dual-phase liquids and level monitoring and/or control issues.

The DPLM instrument includes a first pressure transducer situated beneath the surface of the liquid with a greater specific gravity, which will typically be ground water, at a known distance beneath a level element. The first pressure transducer is a submersible pressure transducer, and is commercially available. A custom-made level element with a float selected so as to float on the surface of the lighter fluid is positioned above the first pressure transducer. The float, which has an embedded magnet, travels on a guide tube with a series of integral reed-switches. The signal from the level element is proportional to the position of the float or the total distance the float is positioned above the bottom of the level element and therefore the total distance above the first pressure transducer, the pressure transducer located in the heaver liquid phase. The level element is custom made to facilitate the first pressure transducer. A second pressure transducer can be deployed above the surface of the liquid if greater accuracy of measurement (as compared to assuming ambient pressure) is desired. The second pressure transducer is either a submersible or splash-proof pressure transducer, and is also commercially available.

The DPLM instrument can be used as a stand alone item, or it can be incorporated into most current art electronics and controls systems.

An advantage of the present invention is that it can be removed from an installation for servicing.

Another advantage of the present invention is that it is portable and can be used at different installations.

Still another advantage of the present invention is that it can be used in deep-well applications and in very small diameter wells.

These and other objects and advantages of the present invention will become apparent to those skilled in the art in view of the description of the best presently known mode of carrying out the invention as described herein and as illustrated in the drawings.

DETAILED DESCRIPTION OF THE INVENTION

Figure 1:
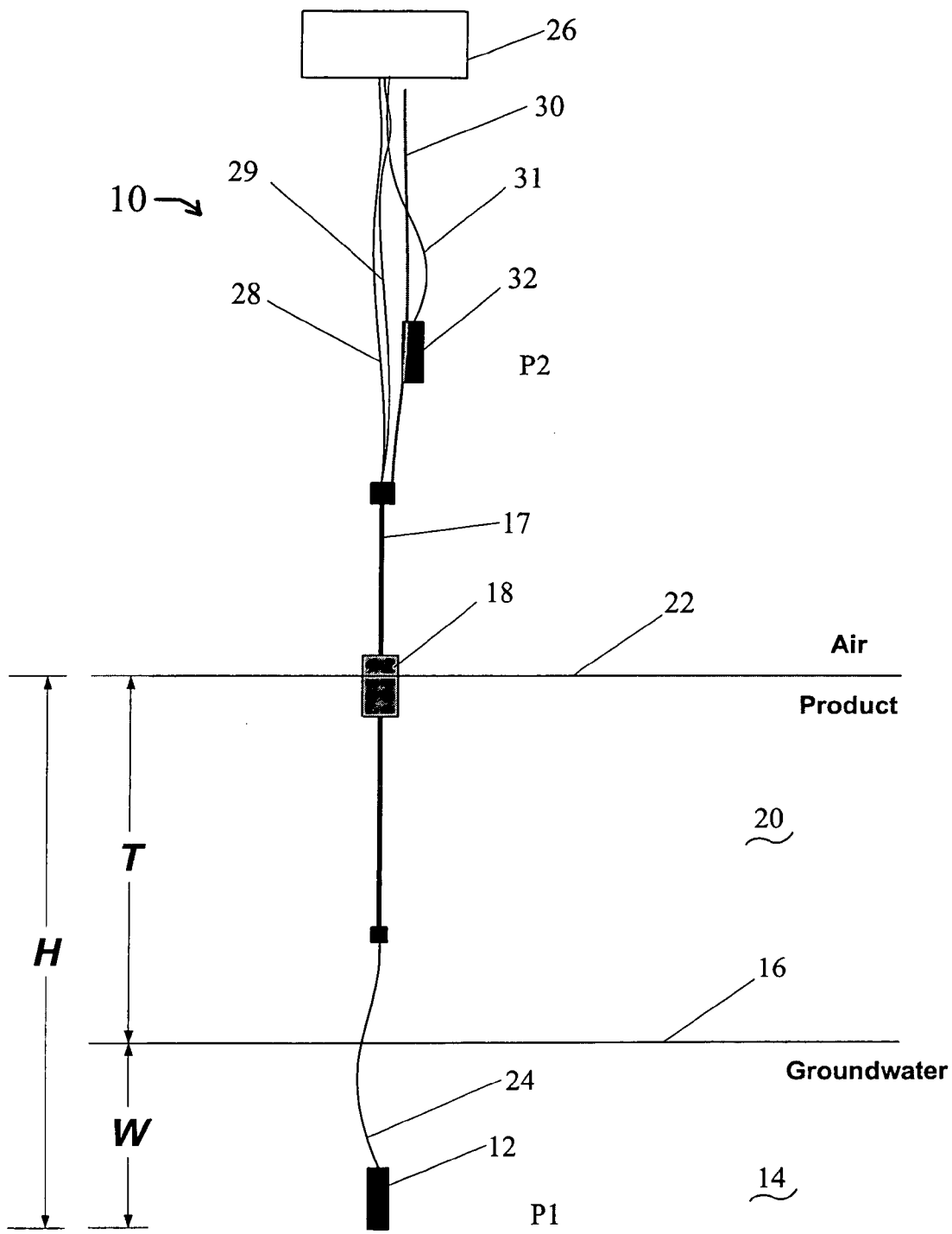
FIG. 1 is a perspective view of the dual-phase level monitoring (DPLM) instrument of the present invention.
Figure 2:
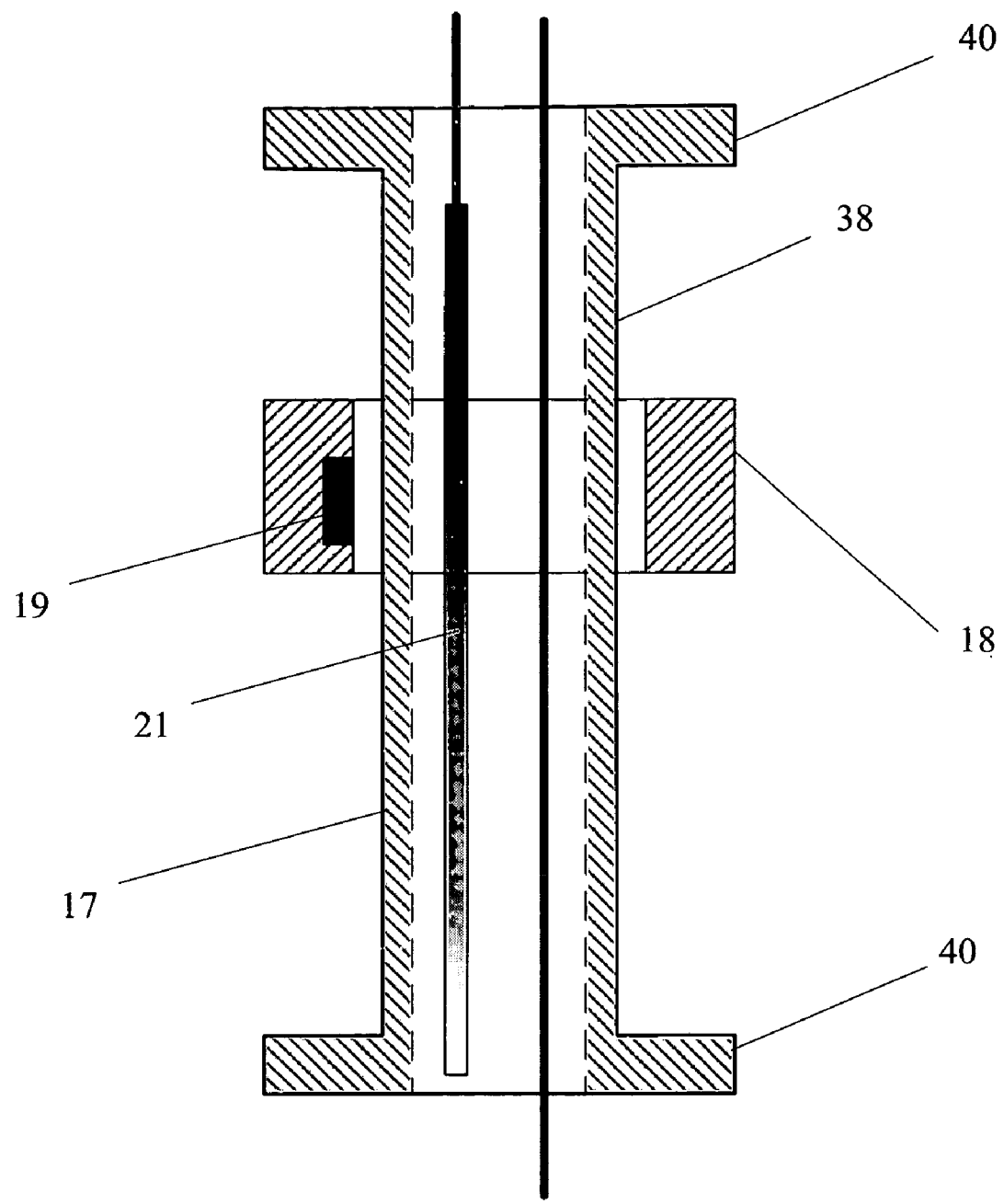
FIG. 2 is a sectional view of the reed-switch level element.
Figure 3:
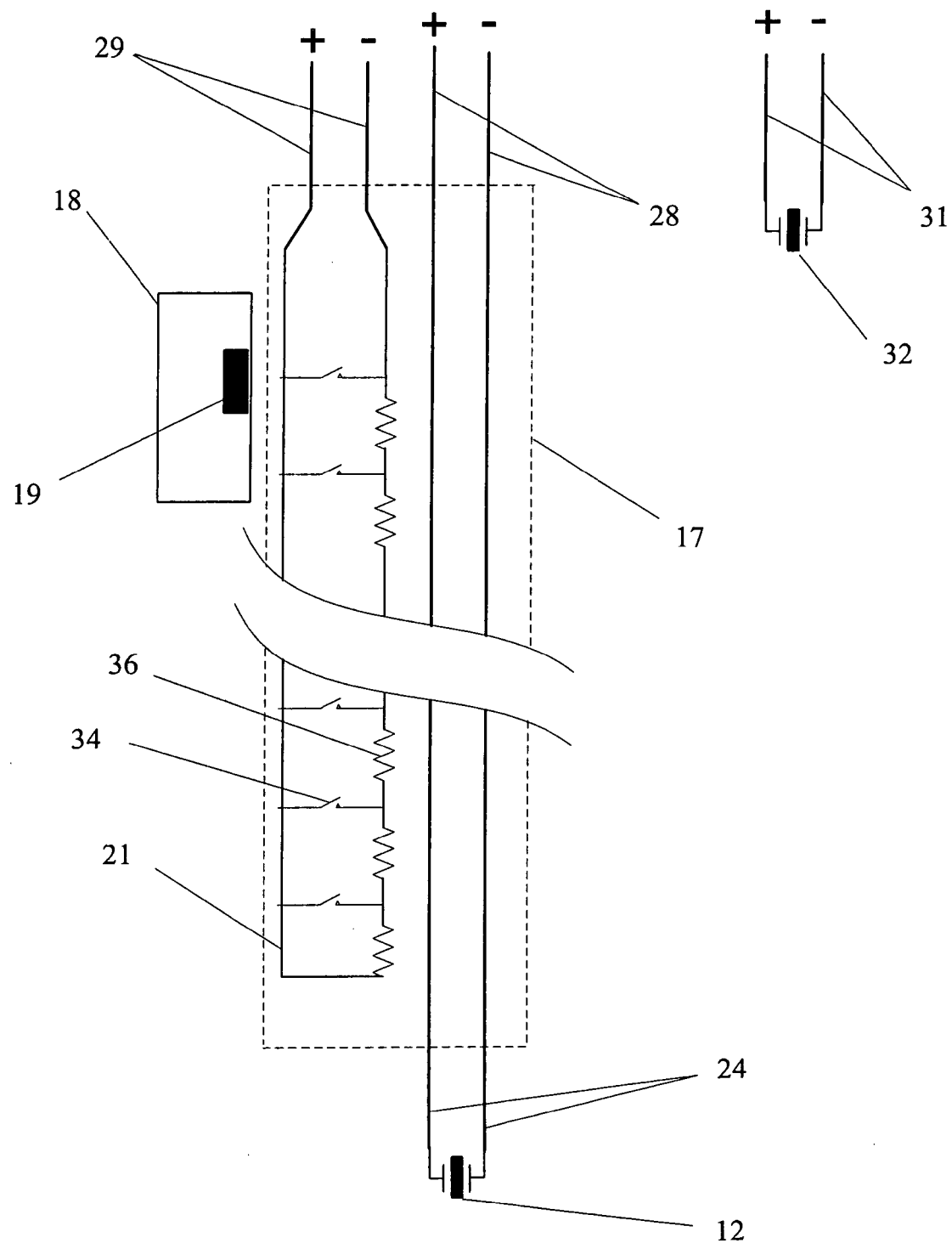
FIG. 3 is an electrical schematic of the DPLM instrument.

The present invention is a method of monitoring dual-phase liquid and interface levels that utilizes a dual-phase level monitoring (DPLM) instrument 10 to continuously monitor a dual-phase reservoir. The method is particularly well suited for groundwater monitoring wells with a light non-aqueous phase liquid (product) and tanks or vessels with dual-phase liquids and level monitoring and/or control issues. The DPLM Instrument 10 provides continuous signals of the level of a top fluid surface and the hydrostatic pressure below the fluid column. The DPLM instrument 10 can be used in wells and vessels operating at a positive or negative pressure relative to atmosphere in addition to being used in wells and vessels that operate at ambient (atmospheric) pressure. An optional configuration also provides a continuous signal for the pressure above the fluid column. When the DPLM instrument 10 is properly configured and positioned, the signals are processed to determine the product layer depth T above the first pressure transducer 12 and the groundwater layer depth W above the first pressure transducer 12. These values, in conjunction with the known position of the DPLM instrument 10 in the well or vessel, allow the dtp (depth-to-product), dtw (depth-to-groundwater), and the thickness of the product layer to be calculated.

The DPLM instrument 10 comprises a first pressure transducer 12 that is suspended in the groundwater 14 beneath the product/groundwater interface 16. The first pressure transducer 12 is a submersible pressure transducer that is commercially available, and can be either a gauge or absolute pressure transducer. A signal cable from the first pressure transducer 12 passes through guide tube seals 21 in a level element 17. The level element 17 includes a float 18 that floats on the surface of the lighter of the two fluids, the product layer 20. The float is constrained to vertical motion on the guide tube 38 of the level element 17 by two mechanical stops 40. The float 18, which includes an integral magnet 19, moves along a guide tube 38 on the main body of the level element 17. The level element 17 also has a reed-switch assembly 21 installed colinearly within the guide tube 38. The reed-switch assembly 21 is comprised of a series of magnetically activated switches 34 and resistors of incremental value 36. As the magnet 19 slides along the guide tube 38 of the level element 17, a signal is generated that is proportional to the total linear distance above the first pressure transducer 12 as indicated by the position of the magnet 19 on the reed-switch assembly 21.

The length of the guide tube 38 on the level element 17 (and the length of travel of the float 18), the physical configuration of the float 18, and the connection between the float 18 and the first pressure transducer 12, are determined by application parameters. Given a specific type of product 20, the material used to form the float 18 is of course chosen so that the float 18 has the proper buoyancy to float on the liquid surface at the air/product interface 22. The length of a first communication link 24 that connects the first pressure transducer 12 and passes through the level element 17 is determined based on the initial depth of the product 20 and the expected variation of the overall hydrostatic head of the aquifer at the site that is expected over the duration of the project. The overall hydrostatic head of the aquifer at the site will vary naturally with changes in the depth of the local water table, and the site may be engineered to vary the overall hydrostatic head as desired. The pressure readings from the first pressure transducer 12 are relayed through the first communication link 24, through a communication link integral to the body of the level element 17 (but electronically isolated from the level element 17) to a power supply, processing, and display unit 26 by a second communication link 28. Level readings from the level element 17, which indicates the position of the float 18 with respect to percent of total travel from the bottom of the level element 17, are relayed to the power supply, processing, and display unit 26 by a third communication link 29. The monitoring components of the system are suspended in the monitored vessel, typically a test well, on a suspension cable 30.

Note that the first pressure transducer 12 can be either an absolute-pressure or relative-pressure transducer. In order to calculate the product layer depth T above the first pressure transducer 12 and the groundwater layer depth W above the first pressure transducer 12, the difference in the pressure above and below the fluid column must be known. If the first pressure transducer 12 is of the relative pressure type, then a hollow tube can be included in the first communication link 24. The tube will open above the body of the level element 17 so that an airway is formed between the first pressure transducer 12 and the air above the fluid column. This will allow the first pressure transducer 12 to provide a pressure signal proportional to the difference between the pressure at location of the first pressure transducer 12 at the bottom of the fluid column and the pressure above the fluid column. The pressure at the first pressure transducer 12 is measured relative to the pressure above the fluid column.

If the first pressure transducer 12 is of the absolute pressure type calibrated to a known reference, then a second pressure value P2, the pressure above the fluid, is required to allow the difference in the pressure between P1 and P2 to be calculated. The P2 pressure value can be supplied in various ways, depending on the degree of accuracy desired in the specific application. The simplest way to assign a value to P2 is to assume ambient air pressure. A more accurate method of determining P2 is to utilize a second pressure transducer 32. The second pressure transducer 32 can of course also be either an absolute or relative pressure transducer. The pressure reading from the second pressure transducer 32 is relayed through a fourth communication link 31 to the power supply, processing, and display unit 26.

If the second pressure transducer 32 is of the relative pressure type, then a hollow tube would be included in the fourth communication link 31 so that an airway is formed between the reference side the second pressure transducer 32 and the atmosphere outside of the well. This would be desirable if the well is under a vacuum or pressure.

Knowing the two pressures, P1 (the pressure at the first pressure transducer 12), and P2 (the air pressure above the fluid), the location of the product/groundwater interface 16 and the air/product interface 22 can be calculated from the following two equations:

$$P1=\{(g/g_c)\times sg_w\times den_w\times W\}+\{(g/g_c)\times sg_p\times den_w\times T\}+P2 \quad \text{Equation 1}$$

$$H=W+T \quad \text{Equation 2}$$

Known values: $sg_p$ and $sg_w$, the specific gravities of the product fluid and of water, respectively; and $g/g_c$, the ratio of gravity to a unit conversion factor to convert mass units to force units.

Measured values; H, the total height of the fluid column above the first pressure transducer 12; P1, the pressures below the fluid column; and P2, the pressure above the fluid column. Note that if the first pressure transducer 12 is of the relative pressure type, the signal from the first pressure transducer will indicate the difference between P1 and P2. Also note that the value for P2 can be assumed.

Manipulation of equations 1 and 2 yields Equation 3:

$$W=\{[\{(P1-P2)/den_w\}/(g/g_c)]-[sg_p\times H]\}\{1/(sg_w-sg_p)\}$$

The DPLM instrument 10 of the present invention provides continuous level monitoring once it has been installed in a well or vessel. The device can be left in place as long as monitoring is desired. However, if other wells in the same area, or at another appropriate location, need to be monitored, the device can be readily transferred. If the user wants to monitor a well or vessel in a removed location, he need only determine the proper value for the specific gravities of the two phases, and locate the first pressure transducer appropriately by lengthening or shortening the first communications link 24. The length of the second communication link 28 and the third communication link 29 would also be modified according to the parameters of the new installation. The maximum thickness of product that can be monitored with a given DPLM instrument 10 depends on the length of the level element 17.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A method of monitoring dual-phase liquid and interface levels comprising the following steps:
   a) removably suspending a monitoring instrument in a site to be monitored,
   b) providing a level element that floats on an upper surface of a product layer of liquid in said site,
   c) providing a first pressure transducer that is connected to said level element at a fixed distance below said level element, said distance being such that said first pressure transducer is suspended in a heavier one of the two liquids being monitored,
   d) continuously monitoring output signals from said first pressure transducer indicating measured fluid pressure,
   e) continuously monitoring output signals from said level element indicating measured fluid pressure, and
   f) comparing said output signals of said first pressure transducer and said level element to a reference pressure to calculate a level of a groundwater and product interface and a thickness of said product layer.

2. The method as defined in claim 1 wherein:
   said reference pressure is assumed to be a known pressure.

3. The method as defined in claim 1 wherein:
   said reference pressure is measured at a reference side of said first pressure transducer, an airway being provided between said first pressure transducer and a position above said upper surface of said product layer.

4. The method as defined in claim 1 wherein:
   said first pressure transducer is in communication with a power supply, processing, and display unit.

5. The method as defined in claim 1 wherein:
   said level element comprises a float with a guide tube, a magnet movable along a length of said guide tube, and a reed-switch installed in a travel path of said magnet; such that said magnet moves along said guide tube in response to a changing fluid level, thereby triggering different levels of resistance in said reed-switch and varying said output signal of said level element.

6. The method as defined in claim 1 wherein:
   said reference pressure is measured by a second pressure transducer positioned above said upper surface of said product layer.

7. The method as defined in claim 6 wherein:
   said second pressure transducer is in communication with a power supply, processing, and display unit.

* * * * *